US00PP13712P29

(12) United States Plant Patent
Hofmann

(10) Patent No.: US PP13,712 P2
(45) Date of Patent: Apr. 8, 2003

(54) NEW GUINEA IMPATIENS PLANT NAMED 'FISIMP 535'

(76) Inventor: Birgit Hofmann, Gassenweg 29, 56170 Bendorf (DE)

( * ) Notice: Subject to any disclaimer, the term of this patent is extended or adjusted under 35 U.S.C. 154(b) by 0 days.

(21) Appl. No.: 10/080,600

(22) Filed: Feb. 22, 2002

(51) Int. Cl.[7] ..... A01H 5/00
(52) U.S. Cl. ..... Plt./318
(58) Field of Search ..... Plt./318

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of New Guinea Impatiens plant named 'Fisimp 535', characterized by its outwardly spreading, rounded and uniformly mounded plant habit; freely branching and freely flowering habit; large rounded light purple-colored flowers with darker purple markings and red purple-colored eye that are positioned above and beyond the foliage; and dark green-colored leaves.

1 Drawing Sheet

BOTANICAL CLASSIFICATION/CULTIVAR DESIGNATION

*Impatiens hawkeri* cultivar Fisimp 535.

BACKGROUND OF THE INVENTION

The present Invention relates to a new and distinct cultivar of New Guinea Impatiens plant, botanically known as *Impatiens hawkeri*, and hereinafter referred to by the name 'Fisimp 535'.

The new Impatiens is a product of a planned breeding program conducted by the Inventor in Hillscheid, Germany. The objective of the breeding program is to develop new moderately compact Impatiens cultivars that flower relatively early with large rounded flowers and attractive flower colors.

The new Impatiens originated from a cross made by the Inventor in July, 1998 of the *Impatiens hawkeri* cultivar Danharras, not patented, as the female, or seed, parent with the *Impatiens hawkeri* cultivar Toga, disclosed in U.S. Plant Pat. No. 10,304, as the male, or pollen, parent. The cultivar Fisimp 535 was discovered and selected by the Inventor as a flowering plant within the progeny of the stated cross in a controlled environment in Moncarapacho, Portugal in March, 1999.

Asexual reproduction of the new cultivar by terminal cuttings taken in Moncarapacho, Portugal, since March, 1999, has shown that the unique features of this new Impatiens are stable and reproduced true to type in successive generations.

SUMMARY OF THE INVENTION

The following traits have been repeatedly observed and are determined to be the unique characteristics of 'Fisimp 535'. These characteristics in combination distinguish 'Fisimp 535' as a new and distinct Impatiens cultivar:

1. Outwardly spreading, rounded and uniformly mounded plant habit.

2. Freely branching and freely flowering habit.

3. Large rounded light purple-colored flowers with darker purple markings and a red purple-colored eye that are positioned above and beyond the foliage.

4. Dark green leaves.

Plants of the new Impatiens can be compared to plants of the female parent, the cultivar Danharras. In side-by-side comparisons conducted by the Inventor in Hillscheid, Germany, plants of the new Impatiens differed from plants of the cultivar Danharras in the following characteristics:

1. Plants of the new Impatiens were taller and not as compact as plants of the cultivar Danharras.

2. Plants of the new Impatiens flowered later than plants of the cultivar Danharras.

3. Flowers of plants of the new Impatiens were light purple in color with darker purple markings and a red purple-colored eye whereas flowers of plants of the cultivar Danharras were white and dark pink bi-colored.

Plants of the new Impatiens can be compared to plants of the male parent, the cultivar Toga. In side-by-side comparisons conducted by the Inventor in Hillscheid, Germany, plants of the new Impatiens differed from plants of the cultivar Toga in the following characteristics:

1. Plants of the new Impatiens were taller and not as compact as plants of the cultivar Toga.

2. Flowers of plants of the new Impatiens were light purple in color with darker purple markings and a red purple-colored eye whereas flowers of plants of the cultivar Toga were light purple in color with a white-colored eye.

Plants of the new Impatiens and the cultivar Fisimp 113, U.S. Plant Patent application filed concurrently, differ in flower coloration.

Plants of the new Impatiens can also be compared to plants of the cultivar Kipulau, not patented. In side-by-side comparisons conducted by the Inventor in Hillscheid, Germany, plants of the new Impatiens differed from plants of the cultivar Kipulau in the following characteristics:

1. Plants of the new Impatiens were larger and not as compact as plants of the cultivar Kipulau.

2. Flowers of plants of the new Impatiens were larger than flowers of plants of the cultivar Kipulau.

3. Flowers of plants of the new Impatiens were light purple in color with darker purple markings and a red purple-colored eye whereas flowers of plants of the cultivar Kipulau were light purple in color with a white-colored eye.

Plants of the new Impatiens can also be compared to plants of the cultivar Kipas, disclosed in U.S. Plant Pat. No. 10,432. In side-by-side comparisons conducted by the Inventor in Hillscheid, Germany, plants of the new Impatiens differed from plants of the cultivar Kipas in the following characteristics:

1. Plants of the new Impatiens were larger and not as compact as plants of the cultivar Kipas.

2. Flowers of plants of the new Impatiens were light purple in color with darker purple markings and a red purple-colored eye whereas flowers of plants of the cultivar Kipas were darker purple in color with less intense red purple-colored eye.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Impatiens. The photograph comprises a side perspective view of a typical flowering plant of 'Fisimp 535' grown in a container.

DETAILED BOTANICAL DESCRIPTION

The cultivar Fisimp 535 has not been observed under all possible environmental conditions. The phenotype may vary somewhat with variations in environment such as temperature and light intensity, without, however, any variance in genotype.

The aforementioned photographs, following observations and measurements describe plants grown in Langley, British Columbia, Canada, under commercial practice in a greenhouse. Rooted young plants were planted in 17.5-cm containers during the spring and the aforementioned photograph and following observations and measurements were taken during the summer about 17 weeks later. During the production of the plants, day temperatures ranged from 21 to 24° C. and night temperatures were about 17 to 18° C. In the following description, color references are made to The Royal Horticultural Society Colour Chart, 1995 Edition, except where general terms of ordinary dictionary significance are used.

Botanical classification: *Impatiens hawkeri* cultivar Fisimp 535.

Parentage:

*Female parent.*—*Impatiens hawkeri* cultivar Danharras, not patented.

*Male parent.*—*Impatiens hawkeri* cultivar Toga, disclosed in U.S. Plant Pat. No. 10,304.

Propagation:

*Type cutting.*—Terminal tip cuttings.

*Time to initiate roots.*—Summer: About 8 to 9 days at 24° C. Winter: About 10 days at 21° C.

*Time to produce a rooted cutting.*—Summer: About 15 days at 24° C. Winter: About 18 days at 21° C.

*Root description.*—Numerous, fibrous, and freely branching; 179D in color.

Plant description:

*General appearance.*—Outwardly spreading, low, rounded and uniformly mounded plant growth habit; freely branching habit, dense and bushy appearance; freely flowering. Moderately vigorous.

*Crop time.*—From a rooted cutting, about 10 to 11 weeks are required to produce finished flowering plants in 12-cm containers.

*Plant height.*—About 20.3 cm.

*Plant diameter or spread.*—About 54.3 cm.

*Lateral branches.*—Quantity per plant: About 14. Length: About 18.5 cm. Diameter: About 8 mm. Internode length: About 3.5 cm. Color: 187A to 187B.

*Foliage description.*—Arrangement: Primarily in whorls. Length: About 13.4 cm. Width: About 4.8 cm. Shape: Elliptic. Apex: Acute to acuminate. Base: Acute. Margin: Serrulate with ciliation. Texture: Smooth, slightly rugose; glabrous. Color: Young and fully expanded foliage, upper surface: 139A. Young and fully expanded foliage, lower surface: 185A. Venation, upper surface: 53A. Venation, lower surface: 187B. Petiole: Length: About 2.5 cm. Diameter: About 3.5 mm. Color: Upper surface: 60A. Lower surface: 187B.

Flower description:

*Flower type and flowering habit.*—Single; large rounded light purple-colored flowers with darker purple markings and red purple-colored eye. Freely and continuously flowering; usually about 6 to 9 flowers and flower buds per lateral branch. Flowers flat and positioned above and beyond the foliage and typically face parallel to the leaf canopy. Petals not persistent; gynoecium persistent. Flowers not fragrant.

*Flower longevity.*—Flowers last about 8 to 9 days on the plant.

*Flowering season.*—Year-round under greenhouse conditions. Plants begin flowering about 9 to 10 weeks after planting.

*Flower buds.*—Length: About 2 cm. Diameter: About 1.6 cm. Shape: Ovoid. Color: 74B to 74C.

*Flower length.*—About 7.1 cm.

*Flower width.*—About 7.25 cm.

*Flower depth.*—About 1 cm.

*Petals.*—Quantity: Five per flower, imbricate. Length: Banner petals: About 3.2 cm. Lateral and base petals: About 3.8 cm. Width: Banner petal: About 5 cm. Lateral and base petals: About 4 cm. Shape: Roughly cordate. Apex: Emarginate. Base: Attenuate. Margin: Entire. Aspect: Mostly flat. Texture: Smooth; satiny. Color: When opening, upper surface: 80C. When opening, lower surface: 74C. Fully opened, upper surface: Ground color, 80C; center of banner petal, 74B, faint. Towards base of petals or eye, close to 57B. Ground color becoming 75A to 75B with subsequent development. Fully opened, lower surface: Between 74C and 80C.

*Spur.*—Quantity: One per flower. Length: About 4.8 cm. Diameter: At apex: About 0.5 mm. At flower: About 3 mm. Aspect: Curved. Color: 53B.

*Peduncles.*—Length: About 5.6 cm. Diameter: About 2 mm. Strength: Strong, flexible. Angle: About 45° from the lateral branch. Color: 187B to 187C.

*Reproductive organs.*—Androecium: Stamen number: Five fused at anthers, hooded; filaments free. Anther length: About 6 mm. Anther shape: Obovate. Anther color: 57C. Pollen amount: Moderate. Pollen color: 8D. Gynoecium: Pistil quantity: One per flower. Pistil length: About 5.5 mm. Stigma color: 57D. Style color: 57D. Ovary: Five-celled. Ovary color: 187A to 187B.

*Seed/fruit.*—Seed and fruit development has not been observed.

Disease/pest resistance: Plants of the new Impatiens have not been observed to be resistant to pathogens and pests common to Impatiens.

It is claimed:

1. A new and distinct cultivar of New Guinea Impatiens plant named 'Fisimp 535', as illustrated and described.

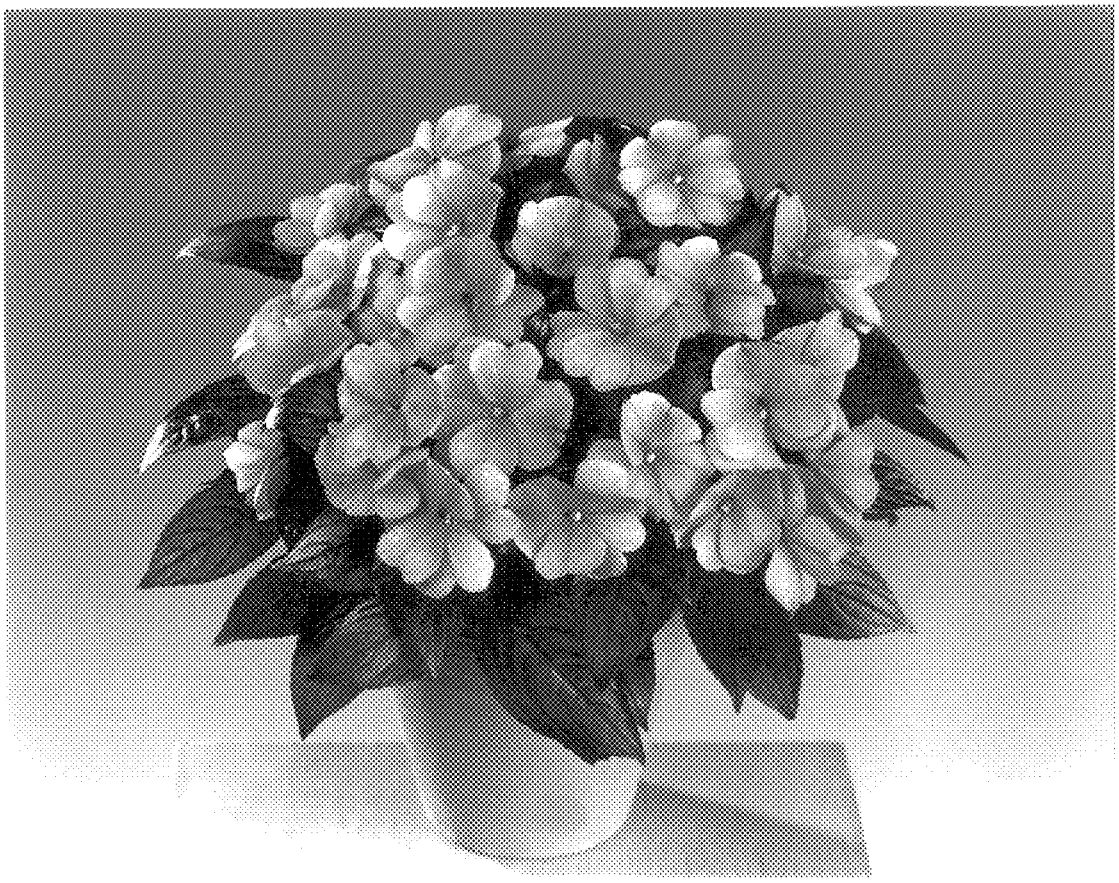

* * * * *